United States Patent
Ikeda et al.

(10) Patent No.: US 8,361,305 B2
(45) Date of Patent: Jan. 29, 2013

(54) METHOD AND DEVICE FOR ANALYZING LIPID COMPONENT CONTAINED IN SERUM

(75) Inventors: Junko Ikeda, Tokyo (JP); Kunihiko Machida, Ehime (JP); Shinki Kojima, Ehime (JP)

(73) Assignee: Panasonic Corporation, Osaka (JP)

( * ) Notice: Subject to any disclaimer, the term of this patent is extended or adjusted under 35 U.S.C. 154(b) by 183 days.

(21) Appl. No.: 12/840,590

(22) Filed: Jul. 21, 2010

(65) Prior Publication Data

US 2011/0024306 A1  Feb. 3, 2011

(30) Foreign Application Priority Data

Jul. 27, 2009  (JP) ................................. 2009-174070

(51) Int. Cl.
*G01N 27/327* (2006.01)

(52) U.S. Cl. ................ 205/777.5; 205/792; 204/403.01

(58) Field of Classification Search ............ 204/403.01, 204/403.14; 205/777.5, 792; 435/11, 19
See application file for complete search history.

(56) References Cited

U.S. PATENT DOCUMENTS 6,146,514 A * 11/2000 Takamura et al. ......... 205/787.5
2004/0265940 A1 * 12/2004 Slater et al. .................. 435/14

FOREIGN PATENT DOCUMENTS

JP  11-89595  4/1999

OTHER PUBLICATIONS

Machine translation of JP 11-89595, Apr. 1999.*
Human translation of JP 11-089595, 1999.*

* cited by examiner

*Primary Examiner* — Kaj K Olsen
(74) *Attorney, Agent, or Firm* — Greenblum & Bernstein, P.L.C.

(57) ABSTRACT

To provide a method of analyzing a lipid component in serum which comprises: a first total acid concentration measurement step of electrochemically measuring the total acid concentration in a serum-containing analyte solution in the presence of a water-soluble quinone derivative; a fatty acid production step of allowing a lipid component in the serum to react with one or more kinds of enzymes which specifically act on the lipid component to produce a fatty acid; a second total acid concentration measurement step of electrochemically measuring the total acid concentration in the serum-containing analyte solution in the presence of the water-soluble quinone derivative; and a lipid component concentration calculation step of calculating the serum concentration of the lipid component based on the total acid concentration measured in the first total acid concentration measurement step and the total acid concentration measured in the second total acid measurement step.

9 Claims, 10 Drawing Sheets

METHOD AND DEVICE FOR ANALYZING LIPID COMPONENT CONTAINED IN SERUM

CROSS REFERENCE TO RELATED APPLICATION

The present application is entitled and claims the priority of Japanese Patent Application No. 2009-174070, filed on Jul. 27, 2009, the disclosure of which including the specification, drawings and abstract is incorporated herein by reference in its entirety.

TECHNICAL FIELD

This disclosure relates to a method and a device for analyzing a lipid component in serum.

BACKGROUND ART

Among methods of detection of a lipid component in serum, enzymatic methods are well known. Many of the generally used enzymatic lipid component detection methods involve a color reaction of generated species with three or four different enzymes along with many reagents for the quantification of a lipid component. For example, for the analysis of the serum concentration of a lipid component such as cholesterol fatty acid esters, glycerin fatty acid esters or phospholipids, it has been known to use enzymatic reactions to quantify a concentration of free fatty acids produced from the lipid component in the serum (see, e.g., Patent Literature 1).

FIG. 1 is a flowchart of the steps for measuring a lipid component in serum by use of the method disclosed by Patent Literature 1. As depicted in FIG. 1, the method requires four steps: first step 11 which measures the total acid concentration in a serum-containing analyte solution, before the production of fatty acid and organic acid from a lipid component); second step 12 which produces fatty acid(s) and organic acid(s) by using an enzyme which specifically acts on the lipid component in serum; third step 13 which measures the total acid concentration in serum by providing a quinone derivative into the analyte solution which contains the fatty acid(s) and organic acid(s) obtained in second step 12; and fourth step 14 which calculates the serum concentration of the lipid component based on the measured values in first step 11 and third step 13.

Citation List

Patent Literature 1: Japanese Patent Application Laid-Open No. 11-89595

SUMMARY OF INVENTION

Technical Problem

The method disclosed in Patent Literature 1 for measuring the concentration of a lipid component in the serum, however, requires an organic solvent in the third step to dissolve a quinone derivative. The use of organic solvent causes serum agglutination as well as reduction in the activity of enzymes which catalyze the producing fatty acid(s) from a lipid component. For these reasons, it is not preferred that second step 12 which involves enzymatic reactions is carried out in the presence of a quinone derivative that requires an organic solvent for dissolution. In the case where the enzymatic reactions in second step 12 are to be performed in the presence of an organic solvent, the analyte solution needs to be filtrated for the removal of agglutinates before the measurement in third step 13, and therefore, the reaction cell for enzymatic reactions and the reaction cell for electrochemical measurement which contains a quinone derivative and an organic solvent need to be separated. Thus, the measurement method disclosed in Patent Literature 1 has the disadvantages of requiring a number of measurement steps and complicated operations.

It is an object of the present invention to provide analysis methods and analysis devices which enable a lipid component in serum to be readily detected in lesser steps than the conventional methods and devices.

Solution to Problem

A method of analyzing a lipid component in serum according to an embodiment includes:

1) a first total acid concentration measurement step of electrochemically measuring the total acid concentration in a serum-containing analyte solution in the presence of a water-soluble quinone derivative;

2) a fatty acid production step of allowing a lipid component in the serum to react with one or more kinds of enzymes which specifically act on the lipid component to produce a fatty acid after the first total acid concentration measurement step;

3) a second total acid concentration measurement step of electrochemically measuring the total acid concentration in the serum-containing analyte solution in the presence of the water-soluble quinone derivative after the fatty acid production step; and 4) a lipid component concentration calculation step of calculating a concentration of the lipid component in the serum based on the total acid concentration measured in the first total acid concentration measurement step and the total acid concentration measured in the second total acid measurement step.

A preferable electrochemical measurement in the presence of a water-soluble quinone derivative, which is conducted in the first and second total acid concentration measurement steps, includes the step of obtaining a voltammogram of analyte solution by voltammetry in each of the first and second total acid concentration measurement steps, and measuring the total acid concentration based on the amount of the difference between "pre-reduction waves" of the water-soluble quinone derivative in the respective voltammograms.

As used herein, the term "the amount of the difference between pre-reduction waves" or equivalent terms may mean the amount of the difference in peak current value or in charge amount between A) a pre-reduction wave of a water-soluble quinone derivative of an analyte solution and either B) a pre-reduction wave of the analyte solution in which total acid concentration is zero or B') a pre-reduction wave of the analyte solution not treated with enzymes. Note that a peak current value of a pre-reduction wave is zero in the case where total acid concentration is zero; thus, in this case, the peak current value of pre-reduction wave of a water-soluble quinone derivative serves as the amount of the difference between the pre-reduction waves.

Because the conventional enzyme-catalyzed lipid component detection methods use a water-insoluble quinone derivative for the electrochemical measurement of the total acid concentration in a serum-containing analyte solution, an organic solvent need to be added to the analyte solution for the dissolution of the water-soluble quinone derivative. The addition of organic solvent, however, causes serum agglutination as well as reduction in the activity of the enzyme used. Thus, it is not preferable to carry out the fatty acid production step in the presence of a quinone derivative which requires an organic solvent for dissolution.

In contrast to the conventional methods using water-insoluble quinone derivatives, the present invention employs water-soluble quinone derivatives far the electrochemical measurement of the total acid concentration in a serum-containing analyte solution. For their high solubility in serum, no organic solvents need to be added to the analyte solution for dissolution. Of course, it is no longer needed to replace the solvent of the analyte solution with an organic solvent after enzymatic reaction, nor is it needed to filtrate the analyte solution as no serum agglutination occurs. In addition, there is no risk that organic solvent inactivate the enzyme. More specifically, the present invention enables the enzyme-catalyzed fatty acid production step to be carried out in the presence of a water-soluble quinone derivative. Thus, an analysis method according to an embodiment requires lesser steps than the conventional methods and enables simple, rapid lipid component analysis.

The lipid component in serum preferably contains a cholesterol fatty acid ester, a glycerin fatty acid ester or a phospholipid, because these substances are clinically important measurement targets.

A method and a device for analyzing a lipid component in serum according to an embodiment electrochemically measures the total acid concentration in a serum-containing analyte solution in the presence of a water-soluble quinone derivative. The water-soluble quinone derivative may be a benzoquinone derivative which can be dissolved into a water-based medium to the concentration of 1 mM or higher. One reason for employing such a benzoquinone derivative is that measurement of a lipid component fails if the amount of the benzoquinone derivative dissolved is smaller than the amount of a serum lipid component to be analyzed. Another reason for this is that the measurement also fails unless the benzoquinone derivative is dissolved in the analyte solution to a concentration significantly higher than those of inherent acids in human serum, such as free fatty acids (normal level: 100-800 µEq/L) and/or lactic acid (normal level in adults: 4-16 mg/dL).

The benzoquinone derivative may have a redox potential in the range of −400 mV to 1,000 mV. If the redox potential is less than −400 mV, it becomes difficult to precisely measure electrochemical signals due to the influence of oxygen dissolved in the solvent of the analyte solution. On the other hand, if the redox potential is greater than 1,000 mV, there arises a fear that the electrodes (e.g., working electrode and counter electrode) in the analysis device dissolve into the medium.

Moreover, the benzoquinone derivative is one which can be used for the electrochemical measurement of a concentration of an acid in the serum. Measuring acid concentration using a benzoquinone derivative means to conduct measurement of acid concentration by voltammetry. Specifically, a voltammogram is obtained; by applying a potential sweep to the analyte solution which contains an acid to be analyzed, a quinone derivative and an electrolyte; and by plotting the current generated as a function of potential. In the measured voltammogram, a pre-reduction wave of the quinone derivative is observed only when the acid existed in the analyte solution. The acid concentration is then found based on the pre-reduction wave of the quinone derivative. Thus, the benzoquinone derivative is required to generate a pre-reduction wave in a voltammogram.

In some embodiments, the benzoquinone derivative may be 2,3-dimethoxy-5-methyl-p-benzoquinone or 2,6-dimethyl-1,4-benzoquinone, because the two compounds are readily dissolved in water-based media to yield higher concentrations and thus serve as stable reagents.

A device for analyzing a lipid component in serum according to an embodiment includes the following members:

1) a first total acid concentration measurement member which electrochemically measures the total acid concentration in a serum-containing analyte solution in the presence of a water-soluble quinone derivative;

2) a fatty acid production member which allows a lipid component in the serum to react with one or more kinds of enzymes which specifically act on the lipid component to produce a fatty acid;

3) a second total acid concentration measurement member which electrochemically measure the total acid concentration in the serum-containing analyte solution in the presence of the water-soluble quinone derivative after the fatty acid production step; and 4) a lipid component concentration calculation member which calculates a concentration of the lipid component in the serum based on the total acid concentration measured in the first total acid concentration measurement step and the total acid concentration measured in the second total acid measurement step.

The analysis device is characterized in that 1) the first total acid concentration measurement member, 2) the fatty acid production member, and 3) the second total acid concentration measurement member use the same reaction cell, more specifically, share one reaction cell. The reaction cell includes a reaction site which retains an analyte solution therein and a pair of a working electrode and a counter electrode which contacts the analyte solution in the reaction site.

The analyte solution in the reaction site is subjected to measurement for a voltammogram by voltammetry, followed by measurement of the total acid concentration based on the amount of the difference between pre-reduction waves of the water-soluble quinone derivative in the measured voltammograms.

The conventional enzyme-catalyzed measurement methods need to use organic solvents since water-insoluble quinone derivatives are used for the electrochemical measurement of the total acid concentration in a serum-containing analyte solution. The use of organic solvents, however, causes serum agglutination as well as reduction in the enzyme activity. Accordingly, in a device for carrying out the conventional enzyme-catalyzed measurement method, a reaction cell in which fatty acid(s) are produced by use of an enzyme which specifically act on a serum lipid component, and a reaction cell in which total acid concentration is measured in the presence of a quinone derivative after the generation of the fatty acids need to be provided separately.

In contrast to the conventional measurement methods which use water-insoluble quinone derivatives, the present invention use water-soluble quinone derivatives for the electrochemical measurement of the total acid concentration in the serum-containing analyte solution. For their high solubility in serum, there is no need to dissolve quinone derivatives into an organic solvent, nor to replace the solvent of the analyte solution with an organic solvent. Thus, a device for carrying out an analysis method according to an embodiment can achieve, in one reaction cell, both enzyme-catalyzed fatty acid generation and electrochemical measurement of total acid concentration in the presence of a quinone derivative. Moreover, the analysis device can use inexpensive electrodes such as carbon paste electrodes since there is no need to use an organic solvent as the solvent of the analyte solution, thus enabling more rapid, inexpensive and simplified measurements than the conventional devices.

Advantageous Effects Of Invention

A method for analyzing a lipid component in serum according to the present invention uses a water-soluble quinone derivative for the electrochemical measurement of total acid concentration in a serum-containing analyte solution, in contrast to the conventional methods which use a water-insoluble quinone derivative. As water-soluble quinone derivatives have high solubility in serum, there is no need to dissolve them into an organic solvent, nor to replace the solvent of the analyte solution with an organic solvent. Thus, even when an enzyme-catalyzed fatty acid generation step is conducted in the presence of a quinone derivative, serum agglutination does not occur and therefore the analyte solution needs not to be filtrated. Of course, there is no risk that organic solvents inactivate the enzyme used. In this way, the analysis method according to the present invention enables rapid, high-precision analysis of a lipid component in lesser steps than the conventional methods.

BRIEF DESCRIPTION ON DRAWINGS

DESCRIPTION OF EMBODIMENTS

A method and a device for analyzing a lipid component in serum according to some embodiments of the present invention will be described below with reference to the drawings.

1. Analysis Method

Figure 1:
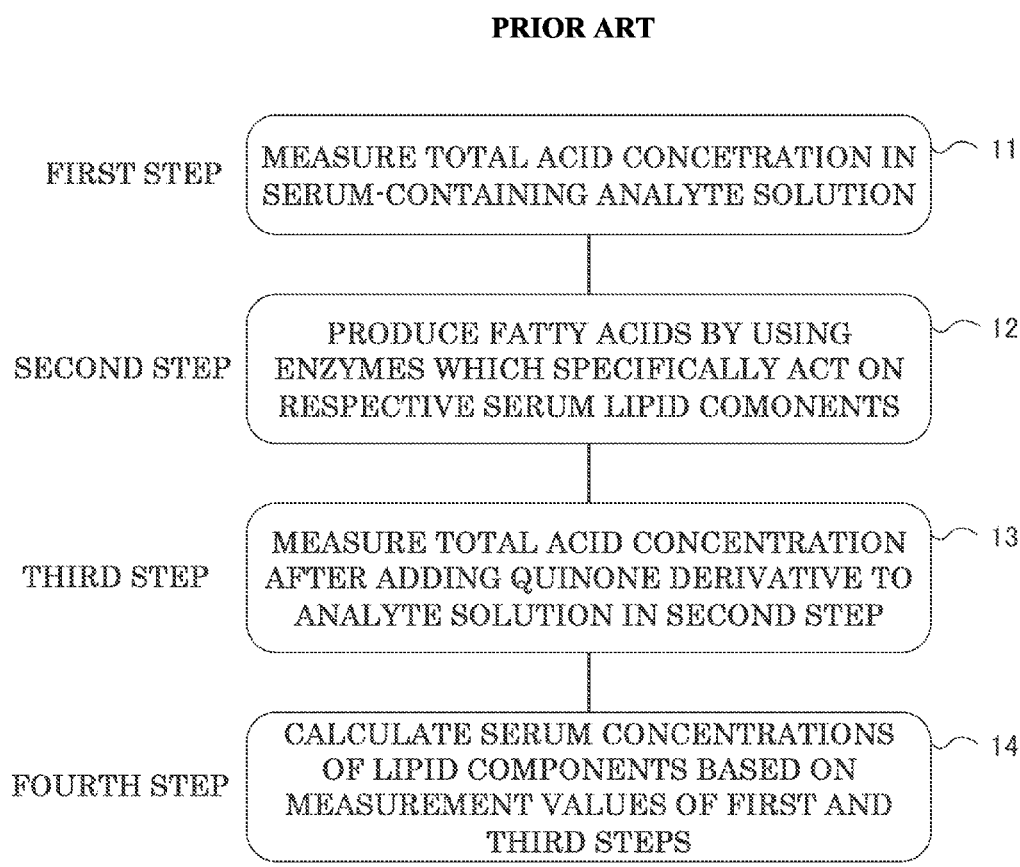
FIG. 1 is a flowchart of the detection procedure according to a conventional measurement method.
Figure 2:
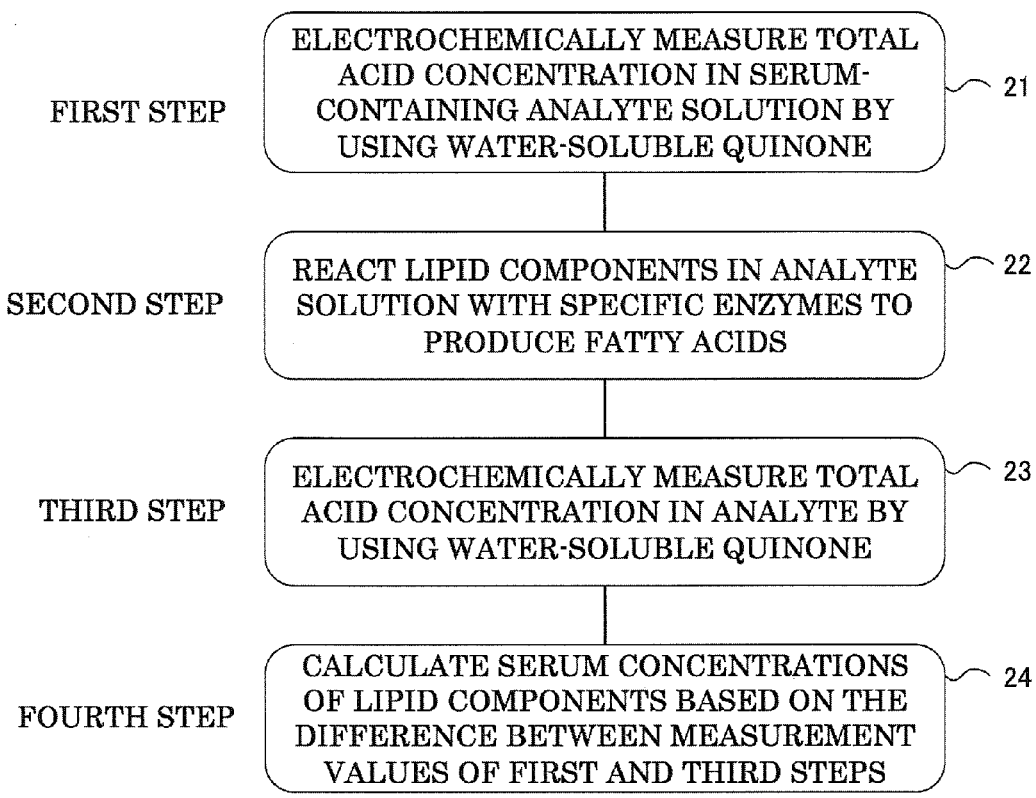
FIG. 2 is a flowchart of the detection procedure according to an embodiment of the present invention.

FIG. 2 illustrates a procedure (first step to fourth step) for analyzing a lipid component in serum according to an embodiment. The procedure includes 1) first step 21 which electrochemically measures the total acid concentration in a serum-containing analyte solution in the presence of a water-soluble quinone derivative; 2) second step 22 which allows a lipid component in the serum to react with an enzyme which specifically acts on the lipid component so as to produce a fatty acid; 3) third step 23 which electrochemically measures the total acid concentration in the serum-containing analyte solution in the presence of the water-soluble quinone derivative after generation of the fatty acids; and 4) fourth step 24 which calculates the serum concentration of the lipid component based on the total acid concentration measured in first step 21 and the total acid concentration measured in third step 23. Each step will be described in detail below.

[First Step 21: Measurement of Total Acid Concentration in Serum-Containing Analyte Solution]

In first step 21, a serum-containing analyte solution is subjected to electrochemical measurement for the total acid concentration in the presence of a water-soluble quinone derivative. More specifically, the total acid concentration is measured by voltammetry.

Firstly, a serum-containing analyte solution is prepared, which contains a water-soluble quinone derivative and electrolyte in addition to a solvent and serum. The presence of an acid (proton donator) in the analyte solution upon electrochemical measurement of the acid concentration causes the quinone derivative to undergo a multiple reaction to generate "a pre-reduction wave in a voltammogram." The electrolyte facilitates electron transfer between analyte species in the solution and the electrode.

The acid concentration in the serum-containing analyte solution is then electrochemically measured. Specifically, prior to producing fatty acid(s) from a serum lipid component by treatment with a specific enzyme (second step 22), a voltammogram is obtained by applying a potential to the serum-containing analyte solution and measuring the current generated during potential application. A characteristic pre-reduction wave is observed in the voltammogram only when an acid exists in the analyte solution. The amount of the difference between pre-reduction waves is then measured for the quantification of the total acid concentration in the analyte solution.

The amount of the difference between pre-reduction waves can be the amount of the difference in peak current value or charge amount between the pre-reduction waves. When distinct peaks of pre-reduction waves (herein after referred to as the "pre-peaks") are observed in the voltammogram, total acid concentration can be found based on the pre-peak height. However, these pre-peaks may or may not be observed depending on the composition of the analyte solution; for example, when the analyte solution contains a buffer solution, it may be difficult to observe the pre-peak in the voltammogram (see embodiment 2). In such a case, total acid concentration can be found based on the difference in charge amount.

In the analyte solution, fatty acids function as a strong proton donator which donates protons to the water-soluble quinone derivative contained in the analyte solution. The quinone derivative which received a proton from a proton donator such as a fatty acid is more prone to reduction than it would be without any proton. Thus, upon voltammetry, quinone derivatives protonated with fatty acid exhibit different reduction waves from those which the quinone derivatives unprotonated with fatty acid exhibit. The reduction wave which is different from a typical reduction wave of a quinone derivative is referred to as a "pre-reduction wave." The pre-reduction wave may appear at positive potentials or negative potentials, with respect to the potential where a typical reduction wave of a quinone derivative appears.

The amount of the difference between pre-reduction waves of a quinone derivative is known to be proportional to the acid concentration in the analyte solution. Thus, precise quantification of total acid concentration is possible by reference to the calibration curve prepared using a set of standard samples of known acid concentration.

In a voltammogram, the potential position where a pre-reduction wave of a quinone derivative appears does not drastically change among different acids (mainly fatty acids) as proton donators. Thus, even when many different types of fatty acids are present in the serum, the total acid concentration in the analyte solution can be precisely measured based on the amount of the difference between pre-reduction waves of the quinone derivative used.

The kind and amount of the water-soluble quinone derivative, electrolyte or solvent may be appropriately selected such that pre-reduction waves of the quinone derivative appear in voltammograms and that the different between the pre-reduction waves is proportional to the acid concentration.

In some embodiments, the water-soluble quinone derivatives can be benzoquinone derivatives such as ortho-benzoquinone derivatives or para-benzoquinone derivatives. Benzoquinone derivatives enable precise analysis of the acid concentration in the analyte solution without having to remove dissolved oxygen from the solution, because their pre-reduction waves appear at significantly different positions than the reduction wave of the dissolved oxygen in the voltammogram.

It is preferable that the water-soluble quinone derivatives used for the measurement have higher solubility in water. As described above, a lipid component cannot be measured unless the amount of the benzoquinone derivative dissolved in the analyte serum is greater than the amount of the lipid component in the serum. As described above, it is considered that human serum contains such acids as free fatty acids (normal level: 100-800 µEq/L) and/or lactic acid (normal level in adults: 4-16 mg/dL). Because measurement of lipid component is impossible unless the benzoquinone derivative is dissolved in the analyte solution to a concentration significantly higher than the serum concentrations of these acids, the quinone derivative preferably has a water solubility of 1 mM or higher.

Although there are only a limited number of quinone derivatives with a water solubility of 1 mM or higher available, 2,3-dimethoxy-5-methyl-p-benzoquinone and 2,6-dimethyl-1,4-benzoquinone (also referred to as "DMBQ") are preferable, for example.

The water-soluble quinone derivatives preferably have a redox potential in the range of −400 mV to 1,000 mV. If the redox potential is less than −400 mV, it becomes difficult to measure precise electrochemical signals due to the influence of oxygen dissolved in the analyte solution. On the other hand, if the redox potential is greater than 1,000 mV, there arises a fear that the electrodes in the analysis device dissolve into the analyte solution.

Among other water-soluble quinone derivatives which meet the above requirements, 2,3-dimethoxy-5-methyl-p-benzoquinone ("DMBQ") is most preferable.

The guideline concentration of the water-soluble quinone derivative in the analyte solution is 1 mM or higher. Measurement is impossible unless the water-soluble benzoquinone derivative is dissolved in the analyte solution to a concentration significantly higher than a concentration of the analyte in the serum. The presumed background acids in human serum are mainly free fatty acids (normal level: 100-800 µEq/L) and/or lactic acid (normal level in adults: 4-16 mg/dL). In view of this, the concentration of the water-soluble quinone derivative is preferably set to 1 mM or higher.

The electrolyte is a water-soluble electrolyte such as potassium chloride or sodium chloride. There are no particular limitations to the electrolyte concentration in the analyte solution as long as electrochemical measurement is possible; it is determined depending on the measurement condition. A typical electrolyte concentration is around 10-200 mM.

The solvent in the analyte solution is preferably a water not including organic solvent. Examples of undesirable organic solvents include water-soluble organic solvents such as alcohols, since organic solvents cause serum agglutination in some cases. When an organic solvent is added in a serum-containing analyte solution, it causes serum agglutination, which necessitates filtration of the analyte solution with a filter prior to electrochemical measurement of acid concentration as the agglutination cause measurement noises during electrochemical measurement. In the present invention filtration is not required because there is no need to add an organic solvent to the analyte solution.

Moreover, using water as the solvent of the analyte solution provides an additional advantage of enabling use of lyophilized agents. This also enables use of inexpensive electrodes such as carbon paste electrodes—which cannot be used in conventional devices as they dissolve into organic solvent—as the electrodes of the analysis device.

[Second Step 22: Production of Fatty Acid from Serum Lipid Component by Enzymatic Reaction]

In second step 22, an enzyme which specifically acts on a lipid component is added in the serum-containing analyte solution to produce fatty acid(s) from the lipid component. Organic acids other than fatty acids can yield depending on the types of lipid component and enzyme used. The enzyme may be added to the analyte solution either before or after electrochemical measurement in first step 21.

When an organic solvent is added in an analyte solution as in the conventional methods, there arises a fear that the organic solvent reduces the activity of the enzyme to be reacted with a lipid component to reduce the measurement sensitivity. For this reason, an enzyme that specifically reacts with a lipid component cannot be used in an analyte solution containing an organic solvent. Specifically, the use of water-insoluble quinone derivatives necessitates the use of organic solvents as in the conventional methods, which prevents an enzyme from reacting with a specific lipid component in the presence of a quinone derivative.

On the other hand, the present invention employs water-soluble quinone derivatives and thus there is no need to added an organic solvent to the analyte solution. This enables a serum lipid component and its specific enzyme to react together in a quinone derivative-containing analyte solution. Specifically, even where serum, enzymes and quinone derivative coexist in the analyte solution, the occurrence of serum agglutination can be suppressed, which eliminates the need to filtrate the analyte solution prior to electrochemical measurement of acid concentration (third step 23). Thus, the present invention enables more rapid, simplified analysis of a serum lipid component than measurement methods that use conventional enzymatic reactions.

The following describes enzymes which specifically act on respective lipid components. One example of the production of free fatty acid(s) from a lipid component is the hydrolysis of a serum cholesterol fatty acid ester by a cholesterol esterase to produce free cholesterol and a free fatty acid. The reaction scheme is given below.

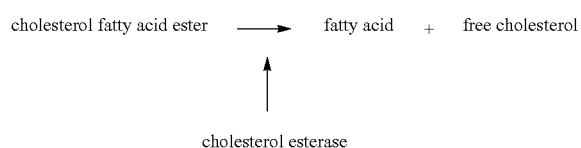

Another example is the hydrolysis of a serum glycerin fatty acid ester by a lipoprotein lipase to produce glycerol and free fatty acids. The reaction scheme is given below. In glycerin fatty acid esters, one, two or three fatty acids are attached to the glycerol by ester bonds. It is known that 90-95% of the serum glycerin fatty acid esters are triglycrides in which three fatty acids are attached to the glycerol by ester bonds. Thus, herein, glycerin fatty acid esters and triglycerine fatty acids are considered to be almost equivalent. In view of this fact, when serum glycerin fatty acid esters are to be analyzed, it is permissible to consider that three free fatty acids are produced from one molecule of a glycerin fatty acid ester.

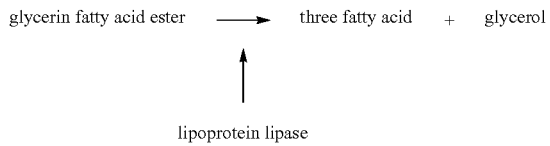

Yet another example is the hydrolysis of a serum phospholipid by phospholipase A to produce a free fatty acid. The reaction scheme is given below. The term "phospholipid" in the formula does not indicate a single chemical compound, but indicates a class of lipids including phosphatidylcholine, sphingomyelin, phosphatidylethanolamine, etc. Most of the phospholipids, including the exemplified phospholipids, yield a free fatty acid by reaction with phospholipase A.

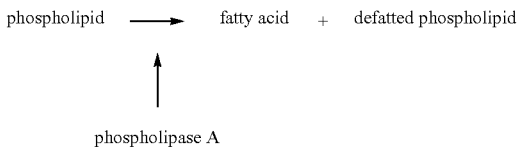

The enzymatic reactions for producing fatty acid(s) from a lipid component are not particularly limited to those given above; any desired reaction can be selected as long as fatty acid(s) can be produced from a lipid component by treatment with a specific enzyme. It should be noted that it is preferable to select single-step fatty acid production reaction schemes in view of simplicity.

There are no particular limitations to the sources of the above enzymes; the enzymes can be derived from any desired source, including animal organs, microorganisms, etc., and genetically modified enzymes produced using DNA synthesized or altered by genetic engineering can also be used. Precautions are that the species produced by enzymatic reactions do not inhibit the subsequent measurement, i.e., measurement of fatty acids (electrochemical measurement in the presence of a water-soluble quinone derivative). The above-exemplified enzymatic reactions were demonstrated to show no particular problems.

All of the enzymes exemplified herein can be purchased ready-made for use. Regarding the use condition of the enzyme (e.g., amount, reaction temperature and reaction time), the parameters presented by the suppliers can be employed without any modification. Alternatively, the parameters can be modified at the user's discretion depending on the intended purpose.

[Third Step 23: Measurement of Total Acid Concentration in the Analyte Solution After Enzymatic Reactions]

In third step 23, after the production of fatty acid(s) from a lipid component by an enzymatic reaction conducted in second step 22, the total acid concentration in the analyte solution is electrochemically measured by voltammetry in the presence of the water-soluble quinone derivative and electrolyte in the same manner as in first step 21.

Because a water-soluble quinone derivative and electrolyte have already been added in the analyte solution in first step 21, they are not necessarily needed to be additionally added in third step 23. However, additional aliquots of the same may be added in third step 23.

[Fourth Step 24: Calculation of the Serum Concentration of Lipid Component]

In forth step 24, the serum concentration of the lipid component in the analyte solution is measured based on the total acid concentration measured in first step 21 and the total acid concentration measured in third step 23. Specifically, the amount of the fatty acid produced from the lipid component is quantified by calculating the difference in total acid amount between first step 21 before enzymatic reactions are conducted and third step 23 after enzymatic reactions are conducted. Quantification of the serum concentration of each type of the lipid components is possible based on the quantified amount of the fatty acid produced from each type of the lipid components.

Because different enzymes act on different lipid components to produce fatty acid(s), quantification is possible for each type of lipid components, specifically for cholesterol fatty acid ester, glycerin fatty acid ester or phospholipid.

2. Lipid Component Analysis Device

An embodiment of an analysis device to which the principle of a serum lipid component analysis method according to an embodiment has been applied will be described below.

Figure 3:
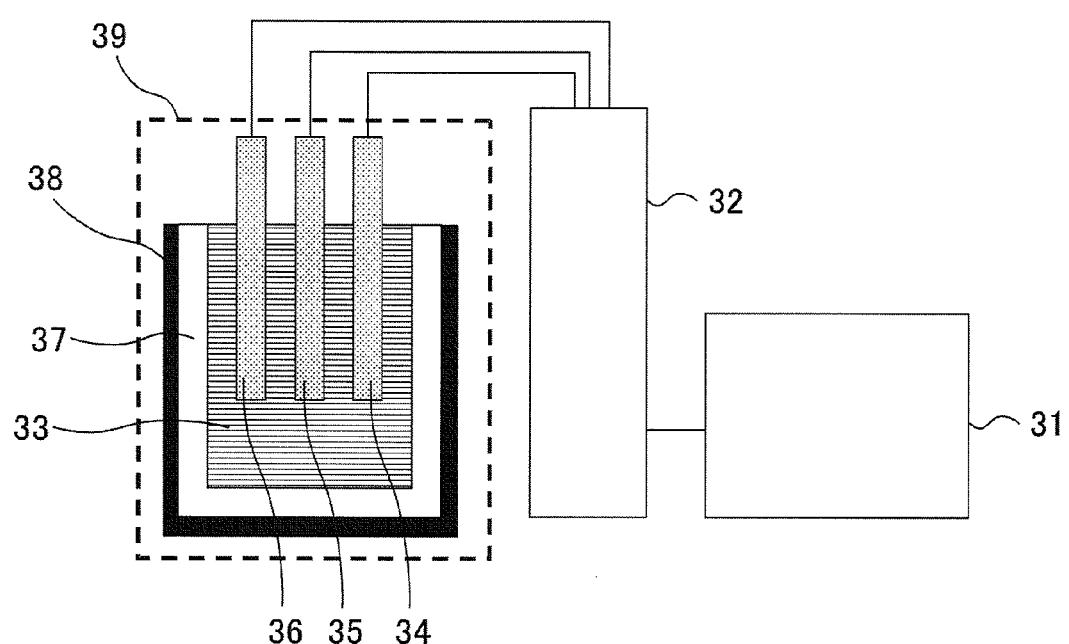
FIG. 3 is a block diagram illustrating the configuration of an analysis device according to an embodiment of the present invention.

FIG. 3 illustrates an example of a device for analyzing a lipid component in serum according to an embodiment. The lipid component analysis device depicted in FIG. 3 is applied to the electrochemical acid concentration measurement method according to an embodiment. The lipid component analysis device includes analysis unit 31, electrochemical measurement instrument 32, and detection unit 39.

Detection unit 39 includes reaction site 33, reference electrode 34, working electrode 35, counter electrode 36, reaction cell 37, and temperature retainer 38. The interior of reaction cell 37 serves as reaction site 33, where reference electrode 34, working electrode 35 and counter electrode 36 are disposed. Reaction cell 37 further includes temperature retainer 38 for retaining the temperature of the solution contained in reaction site 33.

In reaction site 33 of reaction cell 37, the total acid concentration of the analyte solution can be electrochemically measured. In addition, an analyte solution which contains serum and an enzyme which specifically acts on serum lipid component is retained in reaction site 33 so that fatty acid(s) can be produced from the lipid component by an enzymatic reaction. During the enzymatic reaction, the temperature of the analyte solution is retained by temperature retainer 38 so as to facilitate the enzymatic reactions. The enzymatic reactions are often retained at 30-40° C., for example. By allowing an enzymatic reaction to take place in reaction site 33, fatty acid(s) can be produced from a serum lipid component. Many of the enzymes produce fatty acid(s) from specific serum lipid components, and others which act on phospholipids produce organic acid(s) from specific serum phospholipids.

In the analyte solution to be subjected to enzymatic reactions in reaction site 33, a water-soluble quinone, electrolyte and the like may coexist. Thus, the analyte solution can be directly subjected to enzymatic reactions in reaction site 33 after conducting electrochemical measurement of acid concentration in reaction site 33.

The analyte solution which contains fatty acids produced by enzymatic reactions in reaction site 33 of reaction cell 37 is directly subject to acid concentration measurement in reaction site 33. Because water-soluble quinones excepting water-insoluble ones are used, there is no need in the present invention to add an organic solvent to the analyte solution and thus no serum agglutination occurs. This eliminates the need to filtrate the analyte solution prior to the acid concentration measurement to be conducted after enzymatic reaction, so that the analyte solution can be directly subjected to acid concentration measurement.

The electrochemical measurements of the acid concentration of the analyte solution, conducted before and after enzymatic reactions, involve potential sweep of working electrode 35 within a given potential range with respect to reference electrode 34, and plotting the current flowing between working electrode 35 and counter electrode 36 as a function of potential. The electrochemical measurement method of this type is generally referred to as "voltammetry." Electrochemical measurement instrument 32 composed of microcomputers and the like performs the above operations.

Analysis unit 31 detects a pre-reduction wave of a quinone derivative in the current curve measured by electrochemical measurement instrument 32, and then measures the current peak or charge amount corresponding to the pre-reduction wave. The term "pre-reduction wave of a quinone derivative" means a reduction wave of a protonated quinone derivative. The pre-reduction wave may appear at positive potentials or negative potentials, with respect to the potential where a typical reduction wave of a quinone derivative appears. The amount of the difference between pre-reduction waves is proportional to the acid concentration in the analyte solution. Herein, the term "amount of difference" means the amount of the difference in peak current value or in charge amount between pre-reduction waves.

Analysis unit 31 then finds the amount of the difference in peak current value or in charge amount between a pre-reduction wave measured before enzymatic reactions and a pre-reduction wave measured after enzymatic reactions. Based on the difference amount obtained, the amount of acid (mainly fatty acid) produced by an enzymatic reaction and the amount of a lipid component from which the acid(s) were produced are calculated with reference to their calibration curves.

Conventional analysis strategies using enzymatic methods have the drawbacks of low measurement accuracy and prolonged measurement time, as they involve three- or four-step enzymatic reaction followed by measurement the concentration of hydrogen peroxide. By contrast, the serum lipid component analysis device according to this embodiment which employs voltammetry directly measures free fatty acid produced by one-step enzymatic reaction from the serum lipid component, thus enabling simple, rapid, specific, and high-sensitivity quantification of concentration of the serum lipid component.

(Reference Experiment 1)

As reference experiment 1, measurement of citric acid concentration was conducted using 2,6-dimethyl-1,4-benzoquinone as a water-soluble quinone derivative.

1. Reagents

As a water-soluble quinone derivative, 2,6-dimethyl-1,4-benzoquinone (DMBQ; Sigma-Aldrich) was used. The other reagents used are as follows: As an electrolyte, potassium chloride (Nacalai tesque, Inc.) was used, and as an acid to be measured, citric acid (Wako Pure Chemical Industries, Inc.) was used. These reagents were all JIS guaranteed reagents or equivalent reagents, and ultrapure water was used as a solvent to prepare analyte solutions.

2. Preparation of Analyte Solutions 2.55 mL of analyte solutions containing DMBQ (9.7 mM, final conc.), potassium chloride (111 mM, final conc.) and different concentrations of citric acid (0 mM, 0.02 mM, 0.05 mM, 0.1 mM, 0.15 mM, 0.2 mM, 0.49 mM, 0.98 mM, 1.47 mM and 1.96 mM, final conc. (N=5)) were prepared immediately before measurement of citric acid concentration.

3. Measurement of Citric Acid Concentration

An analysis device illustrated in FIG. 3 was prepared which includes as a working electrode a glassy carbon electrode (GCE) with an electrode area of $(1.5)^2\pi$ cm$^2$, as a reference electrode Ag/AgCl (BAS Inc.), and as a counter electrode a Pt wire (1.0 mm diameter). Electrochemical analyzer (BAS100B, BAS Inc.) with BAS100B Windows® Control Software (BAS Inc) was employed. Linear sweep voltammetry was conducted at a scan rate of 5 mV/s toward negative potentials within a potential range of −600 mV to 400 mV (vs. Ag/AgCl).

4. Results

Figure 4:
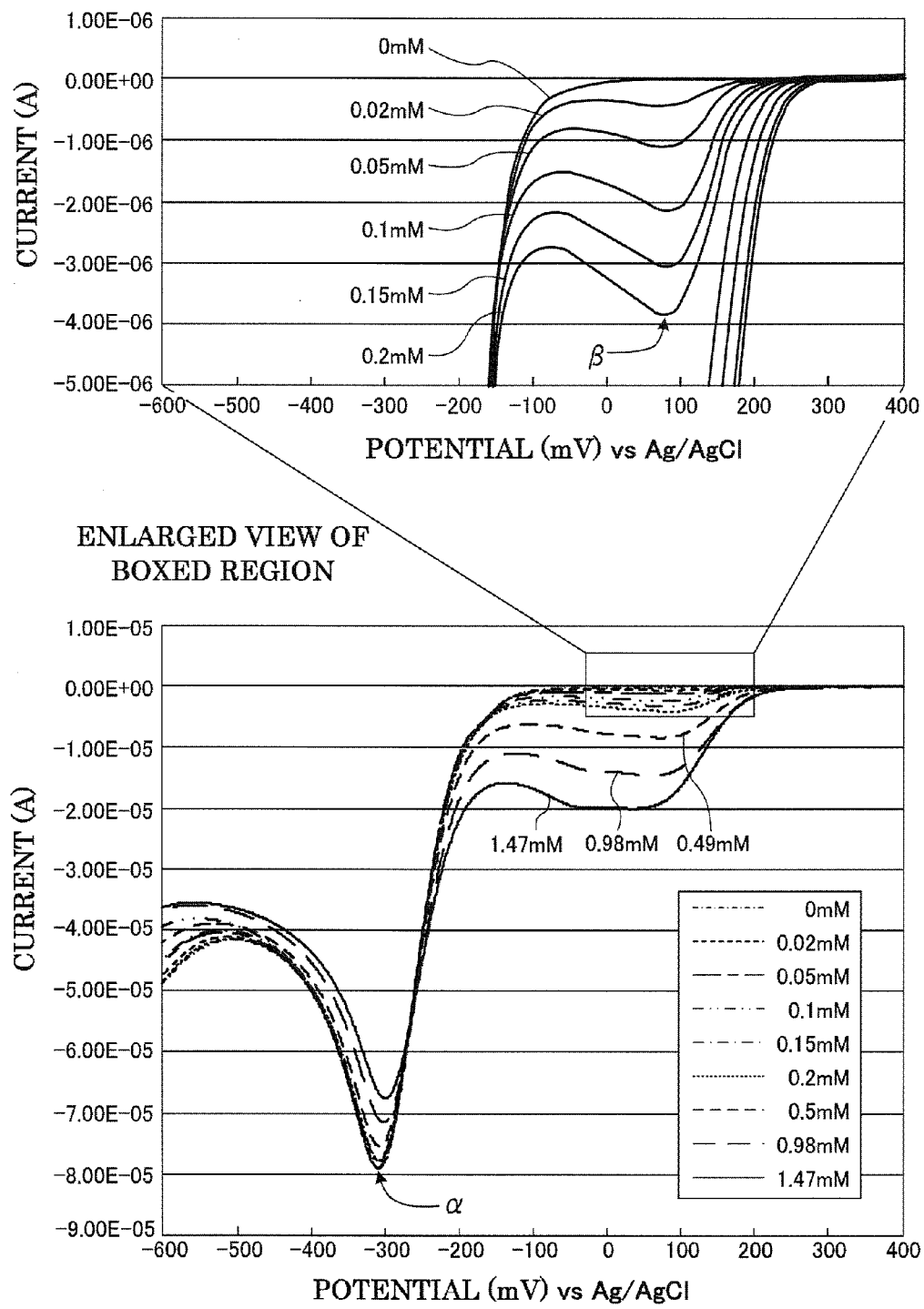
FIG. 4 is a graph of linear sweep voltammograms used for acid measurement using DMBQ (see reference experiment 1)

The graph of FIG. 4 depicts cyclic voltammograms measured for the analyte solutions of different citric acid concentrations. As seen from FIG. 4, it is confirmed that reduction wave peaks α of DMBQ appeared near −300 mV, and that pre-peaks β appeared within a potential range of 50 mV to 150 mV for the samples where the DMBQ concentration is 9.7 mM and citric acid concentration is 0.2 mM or less.

Figure 5:
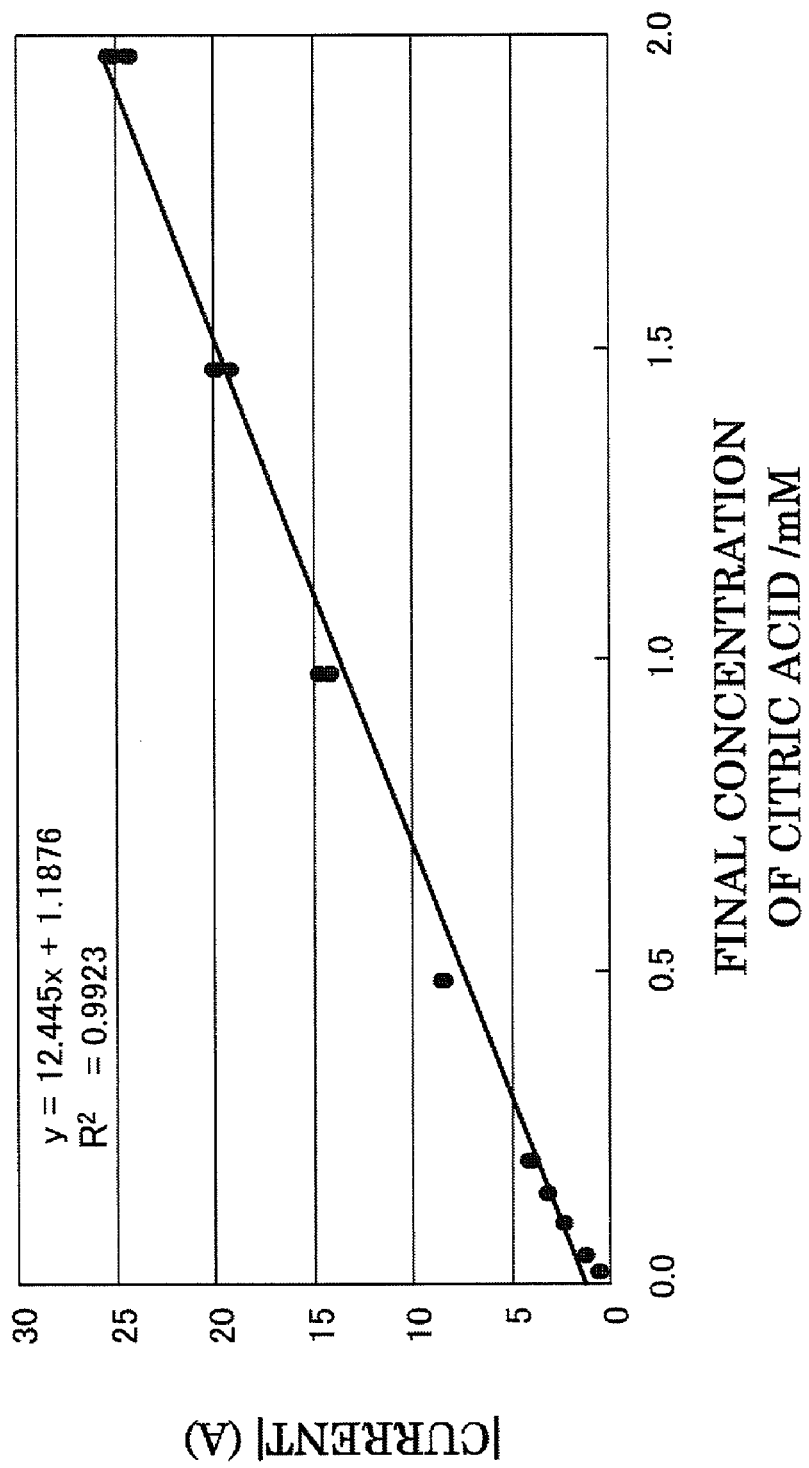
FIG. 5 is a graph depicting the result of the quantification of acid using DMBQ (see reference experiment 1)

The graph of FIG. 5 depicts a plot of the current at the pre-peak of DMBQ (Y axis) vs. citric acid concentration (X axis). Herein, changes in the current values corresponding to the pre-peaks are regarded as the amount of the difference between the pre-reduction waves. In a linear regression analysis, the linear dependence between the peak current value of the pre-reduction wave of DMBQ and citric acid concentration was high ($R^2$=0.99), demonstrating high quantification precision.

In this way, it was established that quantification of citric acid concentrations is possible based on the pre-peaks in the voltammograms obtained by electrochemical measurement in the presence of DMBQ.

(Reference Experiment 2)

As reference experiment 2, measurement of citric acid was conducted using 2,3-dimethoxy-5-methyl-p-benzoquinone as a water-soluble quinone derivative.

1. Reagents

As a water-soluble quinone derivative, 2,3-dimethoxy-5-methyl-p-benzoquinone (Sigma-Aldrich) was used. The other reagents used are the following electrolytes: potassium chloride, citric acid, sodium hydroxide, sodium dihydrogen phosphate, sodium chloride, potassium dihydrogen phosphate and hydrochloric acid (Wako Pure Chemical Industries, Inc.). These reagents were all JIS guaranteed reagents or equivalent reagents, and ultrapure water was used as a solvent to prepare analyte solutions.

2. Preparation of Analyte Solutions 1 mL of analyte solutions containing 2,3-dimethoxy-5-methyl-p-benzoquinone (10 mM, final conc.), different kinds and concentrations of electrolyte (sodium dihydrogen phosphate (4 mM, final conc.), sodium chloride (68 mM, final conc.), potassium dihydrogen phosphate (1 mM) and potassium chloride (1 mM, final conc.)), and different concentrations of citric acid (0 mM, 0.5 mM, 1 mM, 3 mM, 5 mM and 10 mM, final conc. (N=3)) were prepared immediately before measurement of citric acid concentration.

3. Measurement

An analysis device illustrated in FIG. 3 was prepared which includes as a working electrode a glassy carbon electrode (GCE) with an electrode area of $(0.5)^2\pi$ cm$^2$, as a reference electrode Ag/AgCl (BAS Inc.), and as a counter electrode a Pt wire (1.0 mm diameter). Electrochemical analyzer (BAS100B, BAS Inc.) with BAS100B Windows® Control Software (BAS Inc.) was employed. Linear sweep voltammetry was conducted at a scan rate of 50 mV/s toward negative potentials within a potential range of −600 mV to 400 mV (vs. Ag/AgCl).

4. Results

Figure 6:
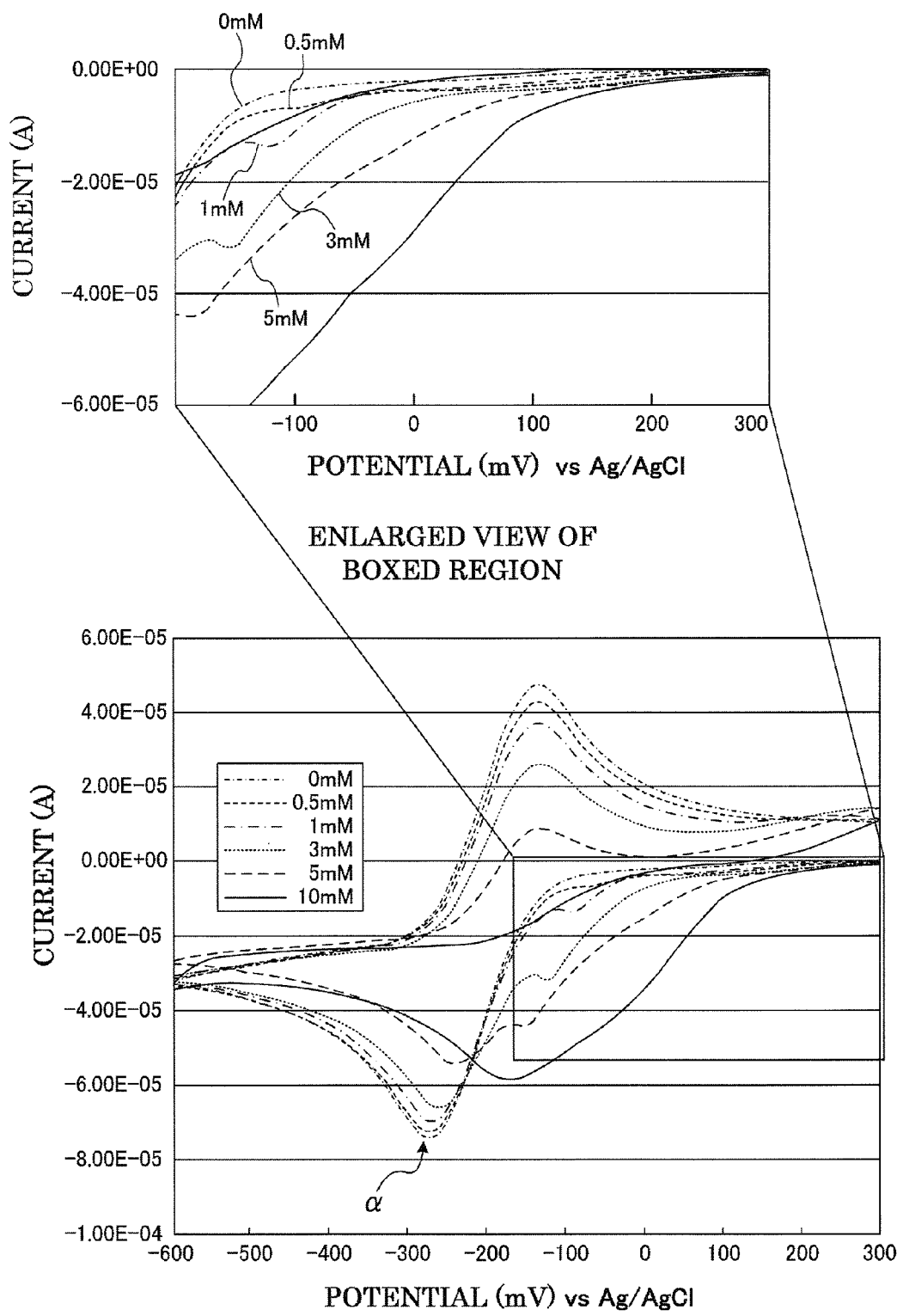
FIG. 6 is a graph of cyclic voltammograms used for measuring acid concentrations using 2,3-dimethoxy-5-methyl-p-benzoquinone (see reference experiment 2)

The graph of FIG. 6 depicts cyclic voltammograms measured for the analyte solutions of different citric acid concentrations. As seen from the enlarged diagram, it is confirmed that quinone reduction wave peaks α appeared near −300 mV, and that pre-peaks β appeared within a potential range of −150 mV to 50 mV for the samples where the concentration of 2,3-dimethoxy-5-methyl-p-benzoquinone is 10 mM and citric acid concentration is 5 mM or less.

Figure 7:
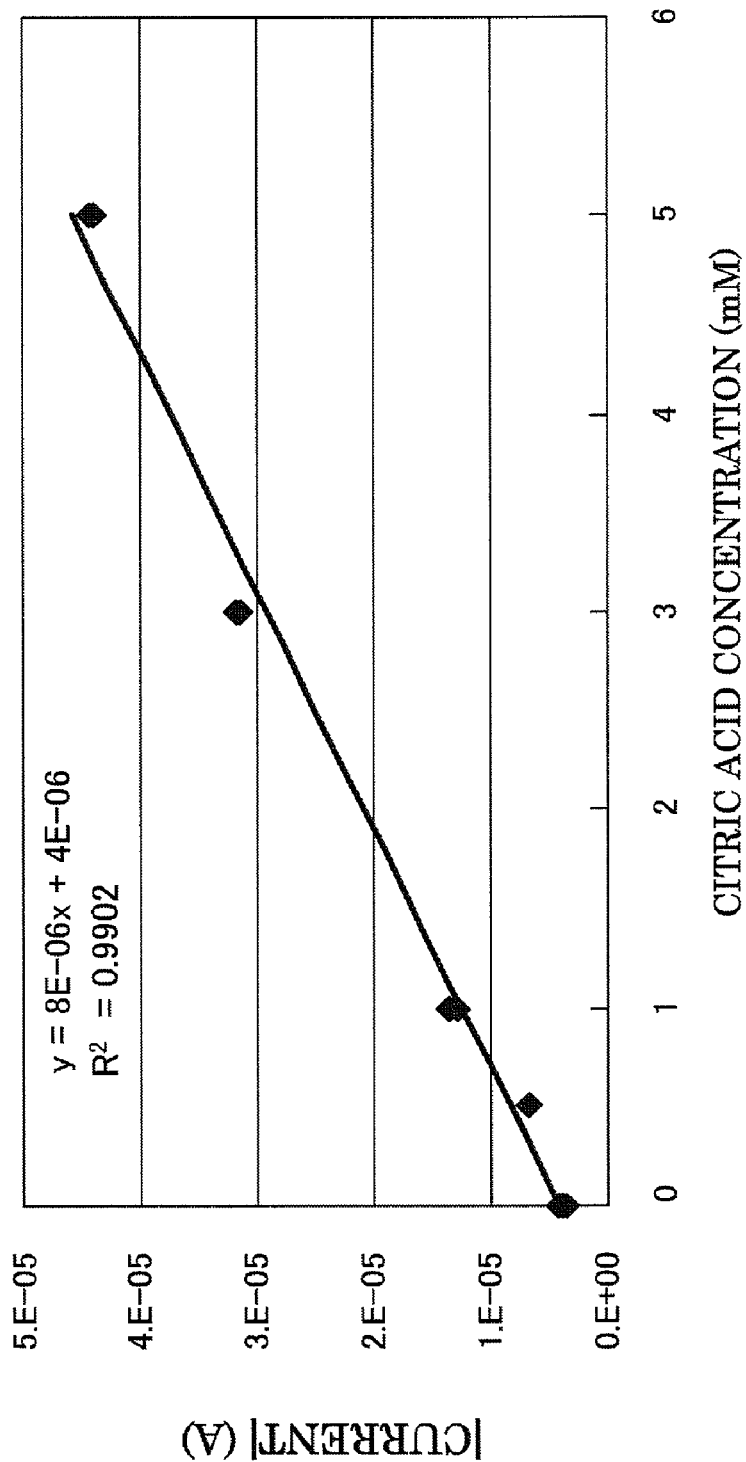
FIG. 7 is a graph depicting the result of the quantification of acid using 2,3-dimetoxy-5-methyl-p-benzoquinone (see reference experiment 2)

The graph of FIG. 7 depicts plots of the current at the pre-peak (Y axis) vs. citric acid concentration (X axis). In a linear regression analysis, high quantification precision ($R^2$=0.99) was demonstrated for the analyte solutions with citric acid concentrations of 5 mM or less.

It was established that quantification of citric acid concentrations is possible by regarding, as the amount of the difference between pre-reduction waves, the amount of the difference in current value between the pre-peaks in the voltammograms obtained by electrochemical measurement in the presence of 2,3-dimethoxy-5-methyl-p-benzoquinone.

(Reference Experiment 3)

As a reference experiment 3, measurement of human serum lipid (TG) was conducted using 3,5-di-tert-butyl-1,2-benzoquinone (DBBQ) as a quinone derivative.

1. Reagents

As a quinone derivative, 3,5-di-tert-butyl-1,2-benzoquinone (DBBQ) (98% pure; Sigma-Aldrich) was used. As an enzyme, lipoprotein lipase (LPL) (LPL-311 from *Pseudomonas* sp.; TOYOBO Co., Ltd.) was used. The other reagents were lithium perchlorate, dipotassium phosphate and potassium dihydrogen phosphate (Wako Pure Chemical Industries, Inc.). These reagents were all JIS guaranteed reagents or equivalent reagents, and ultrapure water was used as a solvent to prepare analyte solutions.

2. Preparation of Analyte Solutions Containing Human Serum TG

A phosphate buffer (pH 7.0) was prepared from dipotassium hydrogen phosphate and potassium dihydrogen phosphate. The phosphate buffer and human serum were mixed together to a final phosphate concentration of 10 mM, and the suspension was allowed to stand overnight at 32° C. An aliquot of the suspension not filtrated was prepared as human serum solution (A), and another aliquot was filtrated through a 0.45 μm-pore size hydrophilic filter (ADVANTEC Co., Ltd.) to prepare human serum solution (B).

To 0.5 mL of each of human serum solutions (A) and (B) was added 1.5 mL of 100% ethanol and the reagents, to prepare 2.5 mL human serum analyte suspensions (50 mM lithium perchlorate, 5 mM DBBQ, final conc.). The suspension from human serum solution (A) not filtrated was prepared as human serum analyte suspension (1), and the suspension from human serum solution (B) filtrated through a hydrophilic filter was prepared as human serum analyte suspension (2).

3. Preparation of Analyte Solutions Containing Fatty Acids Derived from Human Serum TG A phosphate buffer (pH 7.0), a lipoprotein lipase and human serum were mixed together to prepare a suspension (LPL: 18U, phosphate buffer: 10 mM, final conc.), and the suspension was allowed to stand overnight at 32° C. An aliquot of the suspension not filtrated was prepared as human serum TG-derived fatty acid solution (C), and another aliquot filtrated through a hydrophilic filter was prepared as human serum TG-derived fatty acid solution (D).

To 0.5 mL of each of solutions (C) and (D) was added 1.5 mL of 100% ethanol and the reagents, to prepare 2.5 mL human serum analyte suspensions (50 mM lithium perchlorate, 5 mM DBBQ, final conc.). The suspension prepared from solution (C) not filtrated was prepared as human serum analyte suspension (3), and the suspension prepared from solution (D) filtrated through a hydrophilic filter was prepared as human serum analyte suspension (4).

4. Measurement

An analysis device illustrated in FIG. 3 was prepared which includes as a working electrode a glassy carbon electrode (GCE) with an electrode area of $(3.0)^2\pi$ cm$^2$, as a reference electrode Ag/AgCl (BAS Inc.), and as a counter electrode a Pt wire (1.0 mm diameter). Electrochemical analyzer (ALS611A, BAS Inc.) with ALS611A Windows® Control Software (BAS Inc) was employed. Linear sweep voltammetry was conducted at a scan rate of 50 mV/s toward negative potentials within a potential range of −0.2 mV to 0.1 mV (vs. Ag/AgCl).

5. Results

Figure 8:
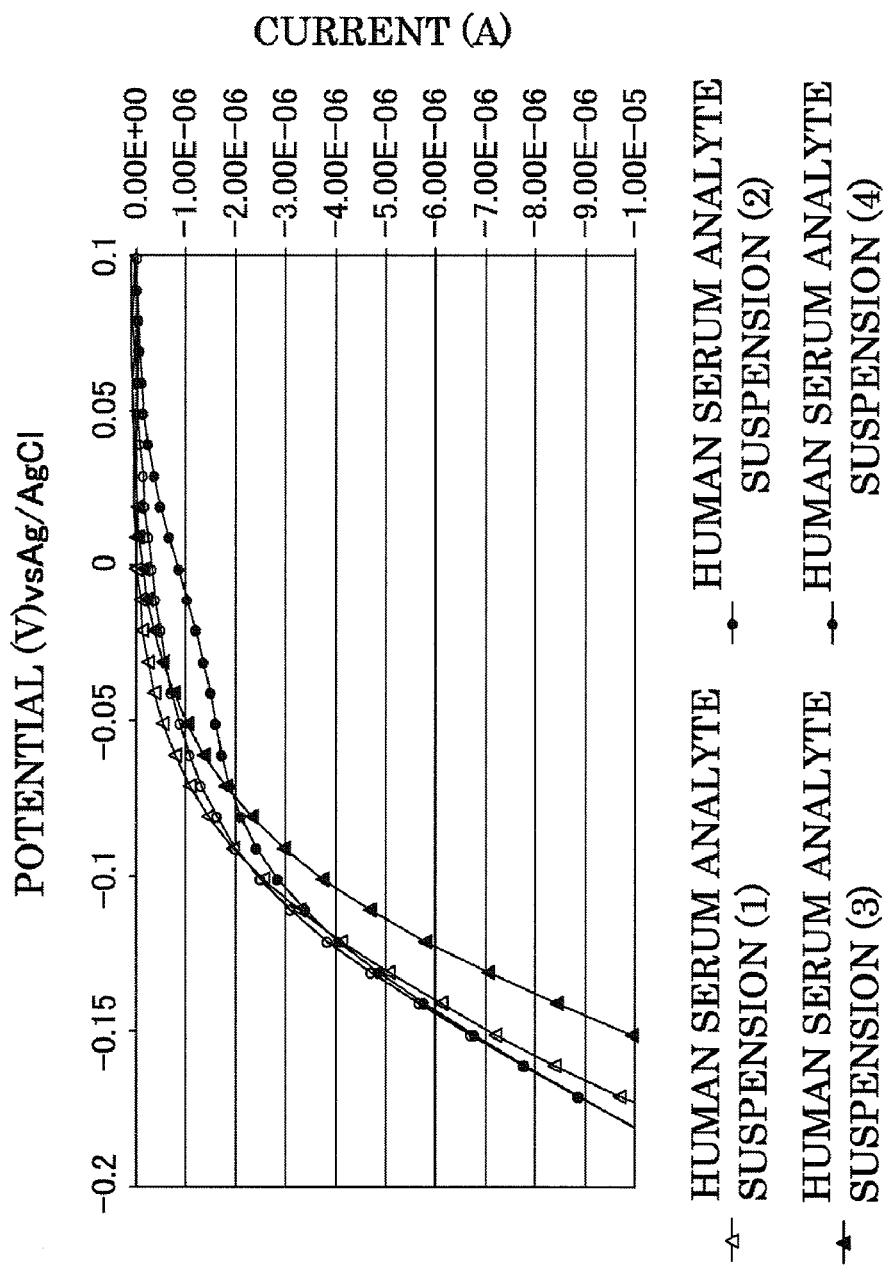
FIG. 8 is graph of linear sweep voltammograms used for measuring the serum concentrations of free fatty acids and total acids (serum free fatty acids plus serum TG-derived fatty acids) using DBBQ (see reference experiment 3)

The graph of FIG. 8 depicts linear sweep voltammograms measured for human serum analyte suspensions (1) to (4). As seen from FIG. 8, the reduction waves measured for non-filtrated human serum analyte suspensions (1) and (3) were largely displaced from each other for example in the potential range of −0.15V to −0.1V. Due to this displacement, stable measurement of the charge amounts for their quinonone pre-reduction waves was not possible. On the other hand, the reduction waves for filtrated human serum analyte suspensions (2) and (4) showed little displacement for example in the potential range of −0.15V to −0.1V. Thus, stable measurement of the charge amounts of their pre-reduction waves in a potential range of around −0.05V to 0V was possible.

For human serum analyte suspensions (1) and (3), the charge amounts of the pre-reduction waves in a potential range of around −0.05V to 0V could not be measured because serum agglutination caused by ethanol made measurement noises which prevented formation of stable reduction waves. For human serum analyte suspensions (2) and (4), on the other hand, stable reduction waves could be obtained because serum agglutination was removed by filtration, thereby enabling the charge amounts for the pre-reduction waves in a potential range of around −0.05V to 0V to be measured. These results demonstrate that electrochemical measurement should be preceded by filtration when an organic solvent is used in the case where a water-insoluble quinone derivative is used.

(Embodiment 1)

As embodiment 1, measurement of human serum lipid (TG) was conducted using DMBQ as a water-soluble quinone derivative.

1. Reagents

As a water-soluble quinone derivative, 2,6-dimethyl-1,4-benzoquinone (DMBQ) (98% pure; Sigma-Aldrich) was used. As an enzyme, lipoprotein lipase (LPL) (LPL-311 from *Pseudomonas* sp.; TOYOBO Co., Ltd.) was used. The other reagents were lithium perchlorate, dipotassium phosphate and potassium dihydrogen phosphate (Wako Pure Chemical Industries, Inc.). These reagents were all JIS guaranteed reagents or equivalent reagents, and ultrapure water was used as a solvent to prepare analyte solutions.

2. Preparation of Human Serum TG-Containing Analyte Solutions

A phosphate buffer (pH 7.0) was prepared from dipotassium hydrogen phosphate and potassium dihydrogen phosphate. The phosphate buffer and human serum were mixed together to a final phosphate concentration of 10 mM, and the suspension was allowed to stand overnight at 32° C. An aliquot of the suspension not filtrated was prepared as human serum solution (A), and another aliquot was filtrated through a hydrophilic filter to prepare human serum solution (B). To 0.5 mL of each of human serum solutions (A) and (B) was added the reagents to prepare 2.5 mL human serum analyte suspensions (50 mM lithium perchlorate, 5 mM DMBQ, final conc.). The suspension from human serum solution (A) was prepared as human serum analyte suspension (1), and the suspension from human serum solution (B) was prepared as human serum analyte suspension (2).

3. Preparation of Analyte Solutions Containing Fatty Acids Derived from Human Serum TG A phosphate buffer (pH 7.0), a lipoprotein lipase and human serum were mixed together to prepare a suspension (LPL: 18U, phosphate: 10 mM, final conc.), and allowed to stand overnight at 32° C. An aliquot of the suspension not filtrated was prepared as human serum TG-derived fatty acid solution (C), and another aliquot filtrated through a hydrophilic filter was prepared as human serum TG-derived fatty acid solution (D). To 0.5 mL of each of solutions (C) and (D) was added the reagents to prepare 2.5 mL human serum analyte suspensions (50 mM lithium perchlorate, 5 mM DMBQ, final conc.). The suspension from solution (C) was prepared as human serum analyte suspension (3), and the suspension from solution (D) was prepared as human serum analyte suspension (4).

4. Measurements

Measurements were conducted as in reference experiment 3.

5. Results

Figure 9:
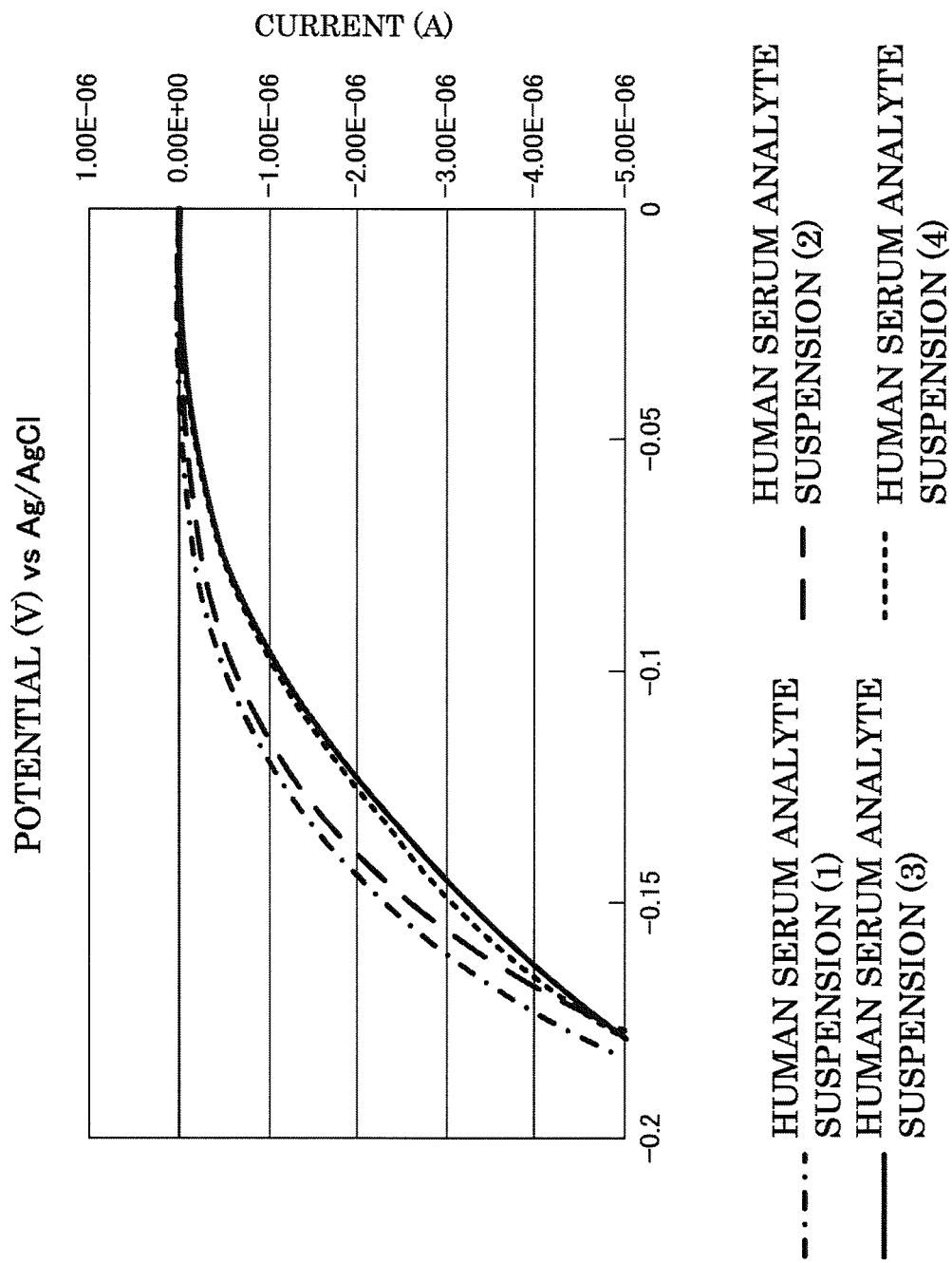
FIG. 9 is a graph of linear sweep voltammograms used for measuring the serum concentrations of free fatty acids and total acids (serum free fatty acids plus serum TG-derived fatty acids) using DMBQ (see embodiment 1)

The graph of FIG. 9 depicts linear sweep voltammograms measured for human serum analyte suspensions (1) to (4). The potential vs. current curves for non-filtrated human serum analyte suspensions (1) and (2) matched and the pre-peaks showed almost the same current response.

Similarly, for non-filtrated human serum analyte suspensions (3) and (4), the potential vs. current curves matched and the pre-peaks showed almost the same current response.

As has been demonstrated above, stable signals were obtained for both of the filtrated and non-filtrated analyte solutions by employing water-based solvents in place of organic solvents while using water-soluble quinone derivatives.

(Embodiment 2)

As embodiment 2, quantification of human serum lipid (TG) was conducted using DMBQ as a water-soluble quinone derivative.

1. Reagents

As a water-soluble quinone derivative, 2,6-dimethyl-1,4-benzoquinone (DMBQ) (98% pure; Sigma-Aldrich) was used. As an enzyme, lipoprotein lipase (LPL) (LPL-311 from *Pseudomonas* sp.; TOYOBO Co., Ltd.) was used. The other reagents were lithium perchlorate, dipotassium phosphate, potassium dihydrogen phosphate, liquid control serum Wako I (TG conc.=86 mg/dL), and liquid control serum Wako II (TG conc.=192 mg/dL) (Wako Pure Chemical Industries, Inc.). These reagents were all JIS guaranteed reagents or equivalent reagents, and ultrapure water was used as a solvent to prepare analyte solutions.

2. Preparation of Human Serum Samples

By mixing liquid control serum Wako I and liquid control serum Wako II, human serum samples containing increasing TG concentrations (86 mg/dL, 112.5 mg/dL, 139 mg/dL, 165.5 mg/dL, and 192 mg/dL) were prepared.

3. Preparation of Human serum TG-Containing Analyte Solutions

A phosphate buffer (pH 7.0) was prepared from dipotassium hydrogen phosphate and potassium dihydrogen phosphate. The phosphate buffer and each human serum sample were mixed together to a final phosphate concentration of 10 mM, and the resultant suspensions were allowed to stand overnight at 32° C. The suspensions were filtrated through a hydrophilic filter to prepare human serum solutions. To 0.5 mL of each human serum solution was added the reagents to prepare 2.5 mL human serum analyte suspensions (A) (50 mM lithium perchlorate, 5 mM DMBQ, final conc.).

4. Preparation of Analyte Solutions Containing Fatty Acids Derived from Human Serum TG The prepared human serum samples were each mixed with a phosphate buffer (pH 7.0) and a lipoprotein lipase to prepare suspensions (LPL: 18U, phosphate: 10 mM, final conc.), and allowed to stand overnight at 32° C. The samples were filtrated through a hydrophilic filter to prepare solutions containing human serum TG-derived fatty acids. To 0.5 mL of each solution was added the reagents to prepare 2.5 mL human serum analyte suspensions (B) (50 mM lithium perchlorate, 5 mM DMBQ, final conc.).

5. Measurement

Measurements were conducted as in reference experiment 3.

6. Results

While distinct peaks of pre-reduction waves were obtained in reference experiments 1 and 2, no distinct peaks of pre-reduction waves were observed in embodiment 2. This is due to the presence of a buffer in the analyte solution; it prevents the clear emergence of a peak of a pre-reduction wave. In such cases, unlike reference experiments 1 and 2, TG concentrations cannot be measured by using the peak current values of the pre-reduction waves as the amount of the difference between the pre-reduction waves.

Instead, linear sweep voltammograms were measured for human serum analyte suspensions not treated with a lipoprotein lipase as well as for human serum analyte suspensions treated with a lipoprotein lipase. The significant difference of the charge amount between the pre-reduction waves in the linear sweep voltammograms was measured as the amount of the difference between the pre-reduction waves.

In embodiment 2, significant pre-reduction wave changes were observed between the linear sweep voltammograms of human serum analyte suspension (A) and the linear sweep voltammograms of human serum analyte suspension (B) in a potential range of OA to $1.2 \times 10^{-6}$ A. Thus, TG concentrations were quantified based on the differences in charge amount in a potential range of 0 A to $1.2 \times 10^{-6}$ A between human serum analyte suspensions (A) and (B).

Figure 10:
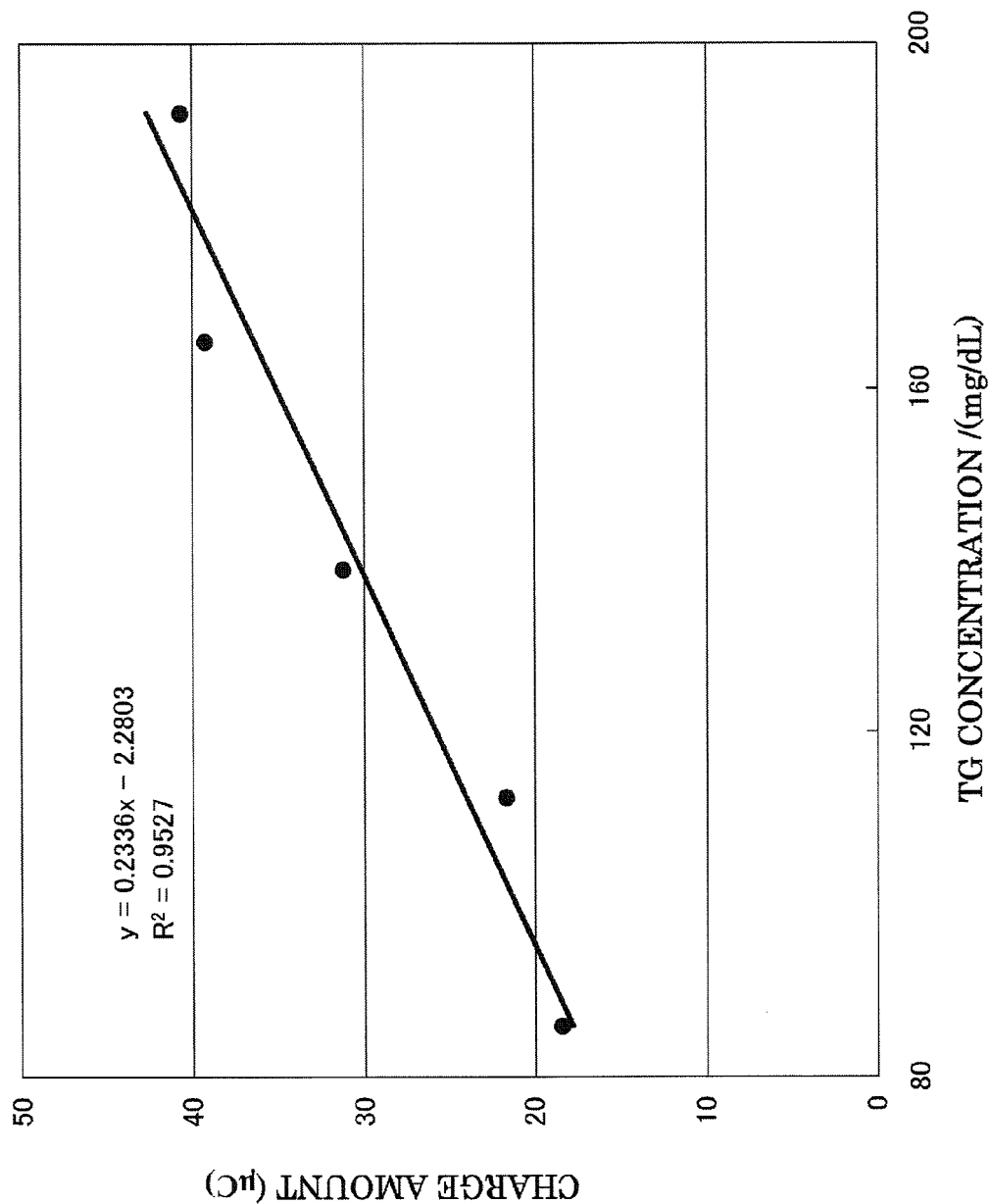
FIG. 10 is a graph depicting the result of the quantification of serum TG concentrations using DMBQ.

FIG. 10 is a graph of charge amount difference (Y axis) vs. serum TG concentration (X axis). In this graph, charge amount increases with increasing TG concentration, demonstrating that quantification of serum TG concentrations is possible based on charge amounts.

Industrial Applicability

A detection method and a detection device according to an embodiment of the present invention are capable of rapid, simple, specific, and high-sensitive analysis of the serum concentration of a lipid component such as cholesterol fatty acid esters, glycerin fatty acid esters or phospholipids, whereby a serum lipid component analysis device for such analysis can be provided at low costs.

| Reference Signs List |
| --- |
| 11. First step |
| 12. Second step |
| 13. Third step |
| 14. Fourth step |
| 21. First step |
| 22. Second step |
| 23. Third step |
| 24. Fourth step |
| 31. Analysis unit |
| 32. Electrochemical measurement instrument |
| 33. Reaction site |
| 34. Reference electrode |
| 35. Working electrode |
| 36. Counter electrode |
| 37. Reaction cell |
| 38. Temperature retainer |
| 39. Detection unit |

What is claimed is:

1. A method of analyzing a lipid component in serum comprising:
 a first total acid concentration measurement of electrochemically measuring the total acid concentration in a serum-containing analyte solution;
 a fatty acid production allowing a lipid component in the serum to react with one or more kinds of enzymes which specifically act on the lipid component to produce a fatty acid after the first total acid concentration measurement;
 a second total acid concentration measurement electrochemically measuring the total acid concentration in the serum-containing analyte solution after the fatty acid production; and
 a lipid component concentration calculation calculating the serum concentration of the lipid component based on the total acid concentration measured in the first total acid concentration measurement and the total acid concentration measured in the second total acid measurement, wherein the first total acid concentration measurement, the fatty acid production, and the second total acid concentration measurement are all conducted in the presence of a water-soluble quinone derivative in the presence of a water solvent in a same reaction cell.

2. The method according to claim 1, wherein the electrochemical measurement in the presence of the water-soluble quinone derivative, which is conducted in the first total acid concentration measurement and in the second total acid concentration measurement, includes:
 obtaining a voltammogram, and measuring the total acid concentration based on the amount of the difference between pre-reduction waves of the water-soluble quinone derivative in the voltammograms.

3. The method according to claim 1, wherein the lipid component in the serum includes a cholesterol fatty acid ester, glycerin fatty acid ester, or a phospholipid.

4. The method according to claim 1, wherein the water-soluble quinone derivative is a benzoquinone derivative.

5. The method according to claim 1, wherein the water-soluble quinone derivative is dissolved into a water solvent to a concentration of 1 mM or higher.

6. The method according to claim 1, wherein the water-soluble quinone derivative has a redox potential in the range of −400mV to 1,000 mV.

7. The method according to claim 1, wherein the water-soluble quinone derivative generates a pre-reduction wave in a voltammogram.

8. The method according to claim 1, wherein the water-soluble quinone derivative is 2,3-dimethoxy-5-methyl-p-benzoquinone.

9. The method according to claim 1, wherein the water-soluble quinone derivative is 2,6-dimethyl-1,4-benzoquinone.

* * * * *